United States Patent [19]

Horrobin et al.

[11] Patent Number: 4,666,701
[45] Date of Patent: May 19, 1987

[54] PHARMACEUTICAL AND DIETARY COMPOSITIONS

[75] Inventors: David F. Horrobin, Surrey, England; Mehar S. Manku; Yung S. Huang, both of Nova Scotia, Canada

[73] Assignee: Efamol Limited, Surrey, England

[21] Appl. No.: 839,228

[22] Filed: Mar. 13, 1986

[30] Foreign Application Priority Data

Mar. 19, 1985 [GB] United Kingdom ............... 8507058

[51] Int. Cl.⁴ ............................................. A61K 27/00
[52] U.S. Cl. .................................................... 424/10
[58] Field of Search ............................................ 424/10

Primary Examiner—Stanley J. Friedman
Attorney, Agent, or Firm—Nixon & Vanderhye

[57] ABSTRACT

Gamma-linolenic acid or dihomo-gamma-linolenic acid for use in the reduction or prevention of gastro-intestinal bleeding and other side effects shown by NSAIDs when administered on a continuing basis, including use in allowing said administration to be replaced by administration of said acid alone in arthritis and other conditions without exacerbation of symptoms.

5 Claims, No Drawings

PHARMACEUTICAL AND DIETARY COMPOSITIONS

FIELD OF THE INVENTION

The invention relates in one aspect to the prevention or reduction of side effects of aspirin and other non-steroidal anti-inflammatory drugs (NSAID), and in another aspect to reduction or elimination of their use.

GENERAL BACKGROUND

NSAID are very widely used in clinical medicine. There is a very large number of drugs in this group including such compounds as aspirin, indomethacin, Diclofenac, Fenoprofen, flufenamic acid, mefenamic acid, flurbiprofen, ibuprofen, ketoprofen, naproxen, phenylbutazone, piroxicam and sulindac. Although compounds with many different structures come into this class it is believed that their common biological mechanism of action is inhibition of the formation of prostaglandins (PGs). The drugs can produce a very wide range of side effects, the most common and consistent of which is gastro-intestinal bleeding. It is believed that the majority of these side effects, including the bleeding, result from the inhibition of PG synthesis. Although they are implicated in inflammation, PGs have many desirable actions, including a poorly understood cytoprotective effect. PGs of the 1-series, derived from DGLA, have particularly desirable actions but unfortunately NSAID inhibit formation of these PGs as well as the 2-series PGs and other compounds, of part desirable, part undesirable effect, formed from arachidonic acid.

The outline of production of 1-series and 2-series PGs in the body is believed to be as shown in the following diagram:

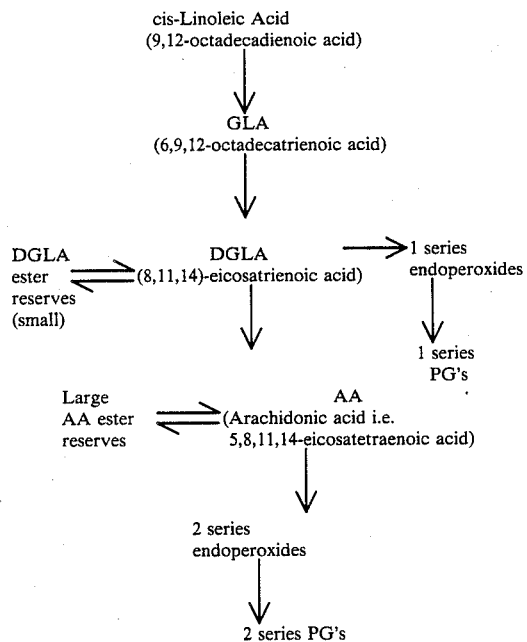

The broad outline of this pathway is well known, and it brings out clearly that a major function of essential fatty acids is to act as precursors for prostaglandins, 1-series PGs being formed from DGLA and 2-series PGs from arachidonic acid. Further, it has recently been found that the 22:4 n-6 acid produced from arachidonic acid gives rise to a series of homo-2-series PGs, though their importance is as yet unknown.

DGLA is the key substance. GLA is almost completely and very rapidly converted in the body to DGLA and so for practical purposes the oral administration of DGLA and GLA amounts to the same thing. DGLA can be converted to a storage form or to PGs of the 1-series or, through arachidonic acid, to PGs of the 2-series.

Considering dietary requirements, it is well known, for example, that linoleic acid cannot be made by the body and so must be taken in the diet. However, it has been generally thought that the body can metabolise linoleic acid to all the other n-6 acids and therefore that provided linoleic acid intake is adequate, no lack of the other n-6 acids will be found.

In previous patent applications (for example, Published European Patent Application No. A 0 003 407, U.S. Pat. No. 4,273,763; Published European Patent Application No. A 0 004 770, U.S. Pat. No. 4,309,415; Published European Patent Application No. 0 019 423, U.S. Pat. No. 4,388,324) it has, however been pointed out that the first enzyme in the pathway, the delta-6 desaturase which, for example, converts linoleic acid to gamma-linolenic acid, is not fully effective in a variety of conditions. The administration of gamma-linolenic acid or dihomo-gamma-linolenic acid or both has been suggested and has been successful in treating a number of clinical conditions.

In the above patent applications attention is primarily paid to the function of essential fatty acids in prostaglandin (PG) metabolism and in particular to their role in securing a proper balance between 1-series and 2-series PGs.

We are, however, becoming increasingly aware of the significance of the essential fatty acids in themselves, in which considerable general interest has been shown in recent years, primarily in the acids of the n-6 series both as such and in relation to prostaglandin metabolism, but also in the acids of the n-3 series. The n-6 acids in particular are required in the body for the structure of membranes in and around cells, being believed to be necessary for maintaining normal flexibility, fluidity and permeability of such membranes.

The pathways of metabolism of the n-6 essential fatty acids and the related n-3 acids sharing, it is believed, common enzymes in the two pathways, are:

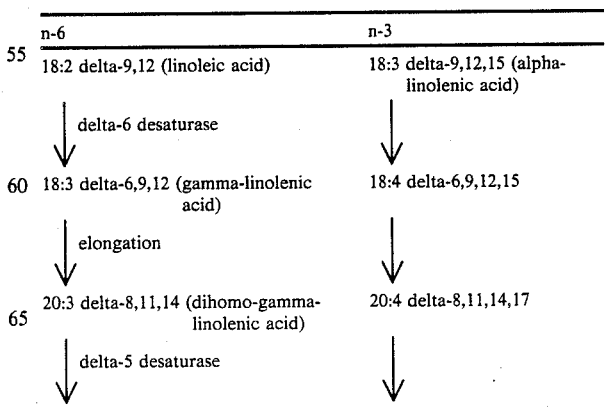

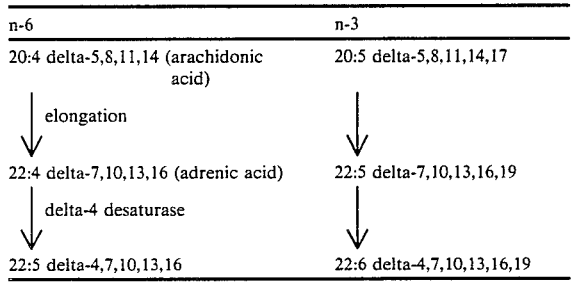

| n-6 | n-3 |
|---|---|
| 20:4 delta-5,8,11,14 (arachidonic acid) | 20:5 delta-5,8,11,14,17 |
| ↓ elongation | ↓ |
| 22:4 delta-7,10,13,16 (adrenic acid) | 22:5 delta-7,10,13,16,19 |
| ↓ delta-4 desaturase | ↓ |
| 22:5 delta-4,7,10,13,16 | 22:6 delta-4,7,10,13,16,19 |

The pathways are not normally reversible nor, in man, are n-3 and n-6 series acids interconvertible.

The acids, which naturally are of the all-cis configuration, are systematically named as derivatives of the corresponding octadecanoic, eicosanoic or docosanoic acids e.g. delta-9,12-octadecadienoic acid or delta-4,7,10,13,16,19 docosahexaenoic acid, but numerical designation such as, correspondingly, 18:2 n-6 or 22:6 n-3 is convenient. Initials, for example, DHA for 22:6 n-3 (docosahexaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature, is to the alpha-acid.

In the body, the n-3 acids are metabolised preferentially and as a result, in plasma for example, levels of alpha-linolenic acid (18:3 n-3) are low and 18:4 n-3 and 20:4 n-3 are in trace amounts only. In contrast the n-6 acids are normally present in moderate amounts, though gamma-linolenic acid (GLA) is at low levels, being apparently converted to dihomo-gamma-linolenic acid (DGLA) more rapidly than its relatively slow production from linoleic acid. In both series the elongation stages in the metabolic pathways are much more rapid than the desaturations.

Generally, as appears from the earlier patent applications referred to, and from other publications by the inventor, the actions of the 1-series PGs and other metabolic products derived from DGLA are almost all either desirable or neutral, but the actions of the 2-series PGs and other metabolic products derived from arachidonic acid are very mixed, some being desirable and some being highly undesirable.

Studies of the interactions between the metabolism of the n-6 acids and that of the n-3 acids have shown that elongation reactions (e.g. GLA to DGLA) are highly efficient and there is very little competition either way. In contrast, the two series of fatty acids are in competition in the desaturation processes. The n-3 fatty acids interfere with both delta-6 and delta-5 desaturation in the n-6 series. This competition seems to occur even when the n-3 fatty acid is not actually a substrate for the enzyme concerned. For example, 20:5 n-3 competitively inhibits the delta-6 desaturation forming GLA from linoleic acid and overall the presence of n-3 fatty acids in a combination leads to some inhibition of the conversion of DGLA to arachidonic acid by the delta-5 desaturase. As a result of the presence of n-3 EFAs, the efficiency of either GLA or DGLA in increasing the ratio of DGLA products (1-series PGs) to arachidonic acid products (2-series PGs) will therefore be increased.

DISCOVERY BEHIND PRESENT INVENTION

We have discovered a new way of preventing or reducing the gastro-intestinal ulceration and bleeding which can occur in the presence of NSAID. We believe that his depends on a hitherto unrecognised biological effect of NSAID and that the mechanism has general relevance to many of the other side effects of NSAID. We have also found a method whereby patients can be withdrawn from treatment with NSAID without any exacerbation of their symptoms and we believe that this will prove of major therapeutic value, since GLA and DGLA are inherently much safer to administer than the NSAIDs.

In experimental work five male and five female normal adult humans in their 20s were each given 1200 mg per day of soluble aspirin for a period of seven days. Blood for measurement (by the method of Pelick et al, cited later herein) of fatty acids in plasma was taken before starting treatment and on the seventh day. No consistent change with regard to many fatty acids occurred but with linoleic acid and its metabolite gamma-linolenic acid (GLA) the following were found:

|  | Linoleic Acid | GLA | Linoleic/GLA Ratio |
|---|---|---|---|
| Total plasma lipid: | | | |
| Before Aspirin | 25.18 ± 4.40 | 0.30 ± 0.27 | 85 |
| After Aspirin | 27.99 ± 5.19 | 0.10 ± 0.19 | 280 |
| Cholesterol ester fraction: | | | |
| Before Aspirin | 52.14 ± 6.48 | 0.55 ± 0.60 | 95 |
| After Aspirin | 56.81 ± 4.26 | 0.16 ± 0.46 | 355 |
| Phospholipid fraction: | | | |
| Before Aspirin | 24.26 ± 4.10 | 0.48 ± 0.09 | 50.5 |
| After Aspirin | 26.48 ± 4.92 | 0.18 ± 0.05 | 147 |

It can be seen that in each case linoleic acid levels went up somewhat, GLA went down substantially and thus the ratio linoleic/GLA increased sharply. This suggests inhibition of the enzyme delta-6-desaturase (d6d) that converts linoleic acid to GLA. Other desaturases may be expected also to be inhibited since they share mechanisms of action in common.

It is concluded that if aspirin is able to inhibit the d6d, then some of the therapeutic effects and the side effects of NSAID relate not to inhibition of PG synthesis directly but to inhibition of EFA desaturation. This has been tested by a study in 30 female rats. 10 control animals received an otherwise fat-free diet contaning 10% safflower oil rich, as regards unsaturated acid, in linoleic acid only. 10 animals received the same diet but also were given 100 mg aspirin intragastrically by gavage twice per day in 2 ml water for seven days. The controls received water only by gavage. 10 further animals received the fat-free diet but supplemented instead of safflower oil with 10% of an evening primrose oil concentrate containing 30% GLA and 65% linoleic acid and also received the same daily aspirin doses as the second group. When the animals were killed, all the controls had normal stomachs with no ulceration. All the 10 animals on the safflower diet had extensive gastric ulceration. Only one of the 10 animials on the GLA rich diet had gastric ulceration, of minor degree. Thus GLA was able to protect the gastric mucosa against the damaging effects of aspirin, indicating that at least some of the side effects of aspirin are related to inhibition of essential fatty acid (EFA) desaturation.

The liver and blood plasma fatty acid composition of the aspirin treated animals was studied. In both liver and plasma in the animals given safflower oil plus aspirin, linoleic acid levels were significantly elevated as compared to animals given safflower oil alone. In contrast, levels of arachidonic acid were significantly reduced indicating inhibition of conversion of linoleic acid to arachidonic acid. The level of 22:5 n-6 (n-6 docosapentaenoic acid), an elongation and desaturation product of arachidonic acid, were reduced to an even greater extent, suggesting that metabolism of EFAs by all three desaturases (d6d, d5d, d4d) had been impaired.

Levels of the n-3 EFAs are very low in rats given a fat-free diet, but those of the last EFA in this pathway, 22:6 n-3 were also significantly reduced by aspirin. This suggests that metabolism of n-3 EFAs was also impaired by aspirin, which is not surprising since it is believed that the n-6 and n-3 EFAs are desaturated and elongated by the same series of enzymes.

We have thus specifically shown that GLA, which as noted above is rapidly converted to DGLA in the body, can provide substantial protection against the gastric effects of aspirin. The protective effect will be improved by providing one or more of the further metabolites of GLA, and/or one or more of alpha-linolenic acid and the metabolites of alpha-linolenic acid in the n-3 series. These metabolites respectively include arachidonic acid, 22:4 n-6, and 22:5 n-6, and 18:4 n-3, 20:4 n-3, 20:5 n-3, 22:5 n-3 and 22:6 n-3.

We have further conducted preliminary studies on the fatty acid compositions of the plasma and liver in rats given indomethacin, mefenamic acid and sodium salicylate. In each case the pattern was similar to that seen in aspirin treated animals, indicating that the effect is not specific to aspirin but characteristic of the general class of NSAID.

In further experimental work GLA alone in the form of evening primrose oil (4 g per day giving 360 mg of GLA per day) was administered to 10 patients with arthritis who were taking NSAIDs. GLA plus EPA (20:5 n-3) in the form of a mixture of 80% EPO plus 20% concentrated fish oil (4 g/day giving 288 mg of GLA and 144 mg of EPA) was given to anotherten patients taking NSAIDs. The fatty acids and the NSAIDs were given together for a period of 3 months and then the NSAIDs were stopped while the fatty acids were continued for a further period of 6 months. During this six month period off NSAIDS, five of the 10 patients on GLA alone and 7 of the 10 patients on GLA plus EPA experienced no worsening of their symptoms and were able to withdraw completely from administration of NSAIDs. Thus it is clear that the administration of GLA alone or in combination with EPA can be used as a method of withdrawing patients from NSAID therapy. Since GLA is rapidly converted in the body to DGLA, DGLA has a similar method of action.

THE INVENTION

The invention thus lies in:

1. The manufacture of medicament for, or a method of, preventing and/or treating side effects of NSAIDs, in particular gastrointestinal bleeding, by use of GLA and/or DGLA.

2. The same, with use of one or more of the other essential fatty acids of the n-6 series or of the essential fatty acids of the n-3 series or both in conjunction with the GLA or DGLA.

3. The same, when applied to reducing or stopping the use NSAIDs in arthritis, and other conditions, without exacerbation of symptoms, replacing said use of NSAIDs by administration of the acids alone.

The invention further lies in a method of preparation of and the use of a therapeutic composition for preventing or reducing the side effects of NSAID, where said composition is made up from GLA and/or DGLA, optionally (as applies above also) with a diluent or carrier and optionally also with the further acids as above, and said composition contains the NSAID itself.

As regards the use of EFAs other than GLA or DGLA above, GLA or DGLA would be expected to be converted along the whole n-6 pathway but some of the steps are known to be slow in many people apart from the effects of NSAID specifically, and direct dietary supplementation with one or more of arachidonic acid, adrenic acid and 22:5 n-6 will thus be of value. Further, the effect of GLA or DGLA will be enhanced by adding in one or more of the n-3 fatty acids, 18:3, 18:4, 20:4, 20:5, 22:5 and 22:6, for the reasons of specific requirements for those acids and/or effect on conversions in the n-6 series discussed earlier. Such acids are preferably but not necessarily used with the higher n-6 acids.

The dosages of each of the fatty acids are 0.1 mg to 20 g, or even 100 g, preferably 100 mg to 1 g daily, or molar equivalent amounts of glycerides, esters or other derivatives. The dosages of the NSAIDs are conventional and are no part of the invention in themselves.

The acids may be used as such or as pharmaceutically acceptable and physiologically equivalent derivatives as, for example, detailed later herein for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al. p. 23, "Analysis of Lipids and Lipoproteins" Ed. Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography on silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

PACKS

If it is not desired to have compositions comprising different active materials together, packs may be prepared comprising the materials presented for separate, or part joint and part separate administration in the appropriate relative amounts, and use of such packs is within the purview of this invention.

DIETARY COMPOSITIONS

The invention is chiefly described in terms of methods of treatment and pharmaceutical compositions, but it will be understood that the gamma-linolenic and other acids, being in the nature of dietary supplements, could be incorporated in a dietary margarine or other foodstuffs for use by those taking NSAID.

AMOUNTS OF GAMMA- AND DIHOMO-GAMMA-LINOLENIC ACIDS

Within the dosages noted earlier, a preferred daily dosage for an adult (weight ca 75 kg) is from 0.1 up to 1, 2, 5 or even 10 g as required gamma-linolenic acid, or equivalent weight (calculated as gamma-linolenic acid) or dihomo-gamma-linolenic acid or physiologically functional derivative of either. Corresponding doses of Oenothera oil containing 8 to 10% of gamma-linolenic acid, are easily calculated.

FORMS AND SOURCES OF GAMMA-LINOLENIC AND OTHER ACIDS

Convenient physiologically equivalent derivatives of gamma-linolenic acid and dihomo-gamma-linolenic acid for use according to the invention, as with the other acids, include salts, amides, esters including glyceride esters and alkyl (e.g. $C_1$ to $C_4$) esters, and phospholipids.

If desired, pharmaceutical compositions may be produced for use in the invention by associating the natural or synthetic acids, as such or as derivatives, with an acceptable pharmaceutical vehicle. It is, however, at present convenient to incorporate at least the gamma-linolenic acid into compositions in the form of an available oil having a high gamma-linolenic acid content, hence reference to "oil" herein.

At the present time known natural sources of oils having a high gamma-linolenic acid content are few (there are no known natural sources of significant amounts of dihomo-gamma-linolenic acid). One source of oils currently available is the seed of Evening Primrose species such as *Oenothera biennis L.* and *Oenothera lamarckiana,* the oil extract therefrom containing gamma-linolenic acid (about 8%) and linoleic acid (about 72%) in the form of their glycerides together with other glycerides (percentages based on total fatty acids). Other sources of gamma-linolenic acids are Borage species such as *Borago officinalis* which, though current yield per acre is low, provide a richer source of gamma-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

As preservative, alpha-tocopherol is added to the oil in a concentration 0.1%.

The seed oil extracts referred to above can be used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon dihomo-gamma-linolenic acid if present.

SOURCES OF OTHER ACIDS

Natural sources of 22:4 and 22:5 n-6 acids include adrenal glands (22:5) and kidneys (22:4) obtained from slaughter houses, and 22:4 in the fat of the American Snapping Turtle. The n-3 acids are available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

PHARMACEUTICAL PRESENTATION

The compositions according to the invention are conveniently in a form suitable for oral, rectal or parenteral administration in a suitable pharmaceutical vehicle, as discussed in detail for example in Williams British Patent Specification No. 1 082 624, to which reference may be made, and in any case very well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera oil may be prepared using albumin to solubilise the free acid.

Advantageously, a preservative is incorporated into the preparations. Alpha-tocopherol in concentration of about 0.1% by weight has been found suitable for the purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

Soft gelatine capsules made by conventional methods are administered against the side effects of aspirin and other NSAID in doses conventional for those drugs in treatment of arthritis or other conditions, as follows:
1. 500 mg capsules of Evening Primrose Oil containing 45 mg GLA, 6/day;
2. 500 mg capsules of borage oil containing 90 mg GLA, 4/day;
3. 100 mg capsules of pure GLA, 4/day;

4. 50 mg capsules of pure DGLA, 6/day;
5. Capsules containing 100 mg GLA, 20 mg 20:4 n-6, 50 mg 20:5 n-3, 5/day;
6. Capsules containing 100 mg GLA, 50 mg 22:4 n-6, 50 mg 20:5 n-3, 50 mg 22:6 n-3, 5/day.

A pack as referred to herein comprises 500 mg capsules of Evening Primrose Oil as above, to be taken 6/day, together with aspirin tablets 300 mg to be taken up to 12/day.

Preparation of compositions as referred to herein is exemplified for example by the preparation of 500 mg capsules of Evening Primrose Oil as above, or for example by addition of 10% by weight of 20:5 n-3 or 22:6 n-3 to Evening Primrose Oil followed by encapsulation, in either case optionally with 300 mg aspirin per capsule, to be taken as above.

In the particular case of treatment of arthritis with the intention of ceasing use of NSAIDs, conventional doses of NSAID are continued for 3 months along with 8/day 500 mg capsules of Evening Primrose Oil (or of the Evening Primrose Oil 80%/concentrated fish oil 20% mixture referred to earlier herein) and the said capsules are continued indefinitely without NSAID intake.

We claim:

1. A method for the reduction or prevention of gastro-intestinal bleeding that aspirin and other non-steroidal anti-inflammatory drugs administered on a continued basis show, said method comprising administering gamma-linolenic acid or dihomo-gamma-linolenic acid to a person at risk of gastro-intestinal bleeding in an amount of 0.1 mg to 20 g daily.

2. A method according to claim 1, wherein said gamma-linolenic acid or dihomo-gamma-linolenic acid is administered as a composition together with an a non-steroidal anti-inflammatory drug in an effective amount.

3. A method according to claim 1 wherein, in order to allow the administration or aspirin or other non-steroidal anti-inflammatory drugs to be reduced or stopped without exacerbation of said gastro-intestinal bleeding, the administration of gamma-linolenic acid or dihomo-gamma-linolenic acid is continued after reduction or cessation of administration of aspirin or other non-steroidal anti-inflammatory drugs.

4. A method according to claim 1 wherein said gamma-linolenic acid or dihomo-gamma-linolenic acid is administered in conjunction with arachidonic acid, adrenic acid or delta-4,7,10,13,16 docosapentaenoic acid in amount of 0.1 mg to 10 g daily.

5. A method according to claim 1 or 2 wherein said gamma-linolenic acid or dihomo-gamma-linolenic acid is administered in conjunction with alpha-linolenic acid, delta-6,9,12,15 octadecatetraenoic acid, delta-8,11,14,17 eicosatetraenoic acid, delta-5,8,11,14,17 eicosapentaenoic acid, delta-7,10,13,16,19 docosapentaenoic acid or delta-4,7,10,13,16,19 docosahexaenoic acid in an amount of 0.1 mg to 10 g daily.

* * * * *